United States Patent
Heo et al.

(10) Patent No.: US 9,903,841 B2
(45) Date of Patent: Feb. 27, 2018

(54) WIRELESS MEASURING SYSTEM BASED ON COCHLEA PRINCIPLE FOR ACQUIRING DYNAMIC RESPONSE OF CONSTRUCTIONAL STRUCTURE

(71) Applicant: Industry Foundation of Konyang University, Nonsan-si (KR)

(72) Inventors: Gwang Hee Heo, Daejeon (KR); Joon Ryong Jeon, Daejeon (KR)

(73) Assignee: Industry Foundation of Konyang University, Nonsan-si (KR)

(*) Notice: Subject to any disclaimer, the term of this patent is extended or adjusted under 35 U.S.C. 154(b) by 380 days.

(21) Appl. No.: 14/631,184

(22) Filed: Feb. 25, 2015

(65) Prior Publication Data

US 2016/0011153 A1 Jan. 14, 2016

(30) Foreign Application Priority Data

Feb. 26, 2014 (KR) .................... 10-2014-0022307

(51) Int. Cl.
| | | |
|---|---|---|
| *G01B 5/28* | (2006.01) | |
| *G01N 29/42* | (2006.01) | |
| *G01N 29/14* | (2006.01) | |
| *G01N 29/44* | (2006.01) | |

(52) U.S. Cl.
CPC ............ *G01N 29/42* (2013.01); *G01N 29/14* (2013.01); *G01N 29/4472* (2013.01); *G01N 2291/0232* (2013.01); *G01N 2291/0258* (2013.01)

(58) Field of Classification Search
CPC .... G01N 29/42; G01N 29/4463; G01N 29/04; G01N 2291/0289; G01N 2291/023
USPC .......................................................... 702/39
See application file for complete search history.

(56) References Cited

U.S. PATENT DOCUMENTS

| | | | |
|---|---|---|---|
| 2002/0043106 A1* | 4/2002 | Board .................... | G01H 1/003 73/579 |
| 2005/0204820 A1* | 9/2005 | Treiber .................. | G01N 29/14 73/649 |
| 2010/0238027 A1 | 9/2010 | Bastianini | |
| 2013/0233081 A1* | 9/2013 | Zhu ....................... | G01N 29/043 73/632 |
| 2015/0226603 A1* | 8/2015 | Hedin .................... | G01H 1/003 702/39 |

FOREIGN PATENT DOCUMENTS

| | | |
|---|---|---|
| KR | 100512123 B1 | 4/2004 |
| KR | 1020060122585 A | 11/2006 |
| KR | 1020100002686 A | 1/2010 |

* cited by examiner

*Primary Examiner* — Stephanie Bloss
(74) *Attorney, Agent, or Firm* — The Webb Law Firm

(57) ABSTRACT

Provided is a wireless measuring system based on a cochlea principle for acquiring a dynamic response of a constructional structure and capable of monitoring and controlling health of the constructional structure in real time by acquiring the dynamic response of the constructional structure in which irregular random vibrations occur, effectively compressing the acquired data, wirelessly transmitting a signal, and analyzing the transmitted signal.

4 Claims, 9 Drawing Sheets

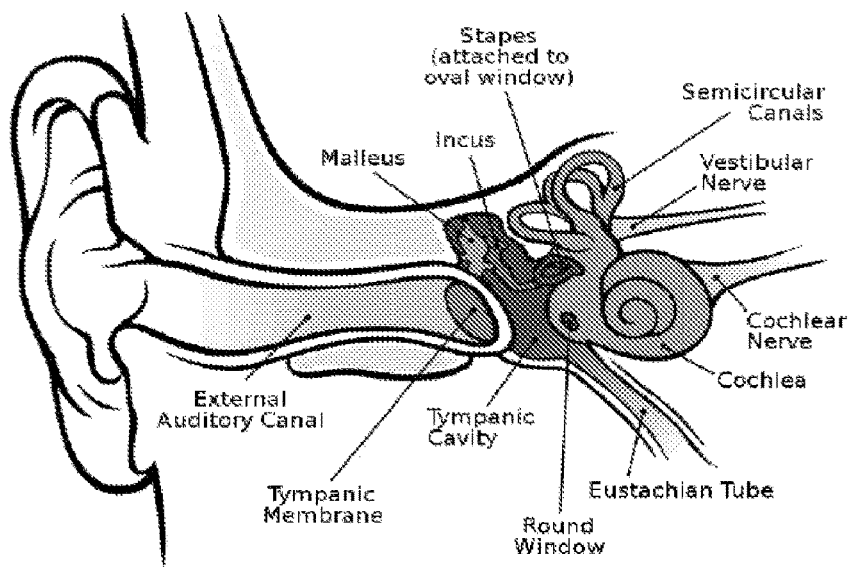
FIG. 3 (A)   Prior Art
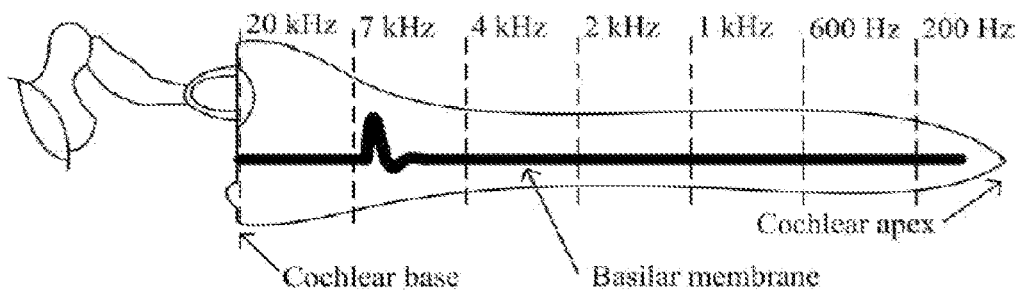
FIG. 3 (B)   Prior Art

FIG. 6

| | | \multicolumn{11}{c}{Number of Filters : 10 , Total Measurement time : 50 seconds} |
|---|---|---|---|---|---|---|---|---|---|---|---|
| | | \multicolumn{11}{c}{Bandwidth(bw)[Hz]} |
| | | 0.0 | 0.1 | 0.2 | 0.3 | 0.4 | 0.5 | 0.6 | 0.7 | 0.8 | 0.9 | 1.0 |
| Interval between Filters(Fsb) [Hz] | 1.0 | | 0.193 | 0.152 | 0.115 | 0.088 | 0.086 | 0.056 | 0.054 | 0.063 | 0.072 | 0.091 |
| | 0.9 | | 0.187 | 0.148 | 0.108 | 0.079 | 0.061 | 0.054 | 0.057 | 0.071 | 0.093 | 0.122 |
| | 0.8 | | 0.186 | 0.140 | 0.100 | 0.072 | 0.060 | 0.062 | 0.077 | 0.103 | 0.140 | 0.185 |
| | 0.7 | | 0.179 | 0.130 | 0.091 | 0.071 | 0.069 | 0.085 | 0.119 | 0.164 | 0.221 | 0.288 |
| | 0.6 | | 0.169 | 0.117 | 0.084 | 0.078 | 0.093 | 0.133 | 0.192 | 0.267 | 0.355 | 0.455 |
| | 0.5 | | 0.164 | 0.109 | 0.087 | 0.103 | 0.152 | 0.230 | 0.332 | 0.453 | 0.389 | x |
| | 0.4 | | 0.157 | 0.111 | 0.120 | 0.184 | 0.293 | 0.436 | 0.607 | x | x | x |
| | 0.3 | | 0.148 | 0.141 | 0.219 | 0.387 | 0.589 | 0.915 | x | x | x | x |
| | 0.2 | | 0.173 | 0.284 | 0.529 | x | x | x | x | x | x | x |
| | 0.1 | | 0.296 | x | x | x | x | x | x | x | x | x |
| | 0.0 | | - | - | - | - | - | - | - | - | - | - |

WIRELESS MEASURING SYSTEM BASED ON COCHLEA PRINCIPLE FOR ACQUIRING DYNAMIC RESPONSE OF CONSTRUCTIONAL STRUCTURE

CROSS-REFERENCE TO RELATED APPLICATION

This application claims priority to Korean Patent Application No. 10-2014-0022307 filed Feb. 26, 2014, the disclosure of which is hereby incorporated in its entirety by reference.

TECHNICAL FIELD

The following disclosure relates to a wireless measuring system based on a cochlea principle for acquiring a dynamic response of a constructional structure. More particularly, the following disclosure relates to a wireless measuring system based on a cochlea principle for acquiring a dynamic response of a constructional structure capable of monitoring and controlling health of the constructional structure in real time by acquiring the dynamic response of the constructional structure in which irregular random vibrations occur, effectively compressing the acquired data, wirelessly transmitting a signal, and analyzing the transmitted signal.

BACKGROUND

Today, infrastructures such as a building, a bridge, a pipe line, and the like, play a very important role in improving the life of the people. Vibrations are continuously caused in these constructional structures for persisting periods of these constructional structures due to various internal/external load conditions, and the constructional structures always behave under the vibrations. Particularly, sudden harmful vibrations such as an earthquake and a gust cause structurally serious damage and injury.

Therefore, it has been required to evaluate health and a state of the structure due to the irregular random vibrations described above, and a technology of efficiently measuring a dynamic response of the structure has been required. This structure is called a structural health monitoring (SHM) technology, and importance thereof has been gradually increased.

When the SHM technology is used to monitor the state of the structure in real time and find a damaged position in advance, stability of the structure may be secured, and a large accident that may occur may be prevented in advance. In addition, a time and a cost required for repairing and reinforcing the structure are also decreased.

Currently, an SHM system transmits a measurement result to a main computer, and the main computer monitors and analyzes the measurement result to evaluate the health and the state of the structure. However, response data of the structure are simply transmitted, such that an immediate action or effective management is not performed.

A technology for solving the problem as described above has been disclosed in Korean Patent Laid-Open Publication No. 2010-0002686 entitled "System for Measuring and Controlling Structure Using Bidirectional Communication Function" and published on Jan. 7, 2010. This Related Art Document relates a system for measuring and controlling a structure capable of monitoring and actively controlling a state of each structure such as a bridge, a building, or the like, using a bidirectional communication function, and is shown in FIG. 1.

However, in this Related Art Document, a sensor system installed in the structure and a main computer acquiring and analyzing data output from the sensor system are connected to each other in a wired scheme. Therefore, a volume of cables required for communication is large and a large cost is required, such that a cost required for building a system is significantly increased.

In addition, an invention of the same technical field as that of the present invention has been disclosed in Korean Patent No. 0512123 entitled "Structure Monitoring System Using Smart Wireless Measuring System" registered on Aug. 26, 2005. This Related Art Document relates to a structure monitoring system using a smart wireless measuring system, and more particularly, to a structure monitoring system that includes a self-adjusting function capable of complementing a problem of an outbreak situation in a measuring function of a sensor itself by applying a smart technology to a sensor used in a monitoring technology of each structure such as a bridge, a building, or the like, a small storage device for preventing loss of data in an emergency situation, a central processing unit (CPU), and a power maintaining function, may perform wireless self-obtained measurement, analyzes and evaluates measured data so as to be appropriate for structural characteristics of an infrastructure to protect the structure itself from damage or an influence of an external environment, and actively copes with any emergency situation to minimize damage and safely protect human life. In addition, this Related Art Document relates to a monitoring system developed as compared with an existing monitoring system of an infrastructure, that is, a state evaluation monitoring system of an infrastructure.

U.S. Patent Application Publication No. 2010-0238027 entitled "Device for Monitoring the Health Status of Structures" and published on Sep. 23, 2010, which is an invention of the same technical field as that of the present invention, relates to a device for monitoring a health status of structures installed at a selected position of the structures and having improved reliability and performance. The device for monitoring a health status of structures is configured to include data collecting, processing, and storing media, and network wireless connection systems widely connected to each other, and continuously receives power by a power supply system including at least two power supplies. Particularly, the device for monitoring a health status of structures further includes a sensor acquiring response data that always behave or non-synchronous trigger data, and further includes a data processing medium for compressing data and automatically detecting a structural deviation using a self-training neural data processing algorithm.

In order to efficiently perform health monitoring, as many sensors as possible are required. Particularly, in the case in which the SHM system is built in a large structure having many measuring points for acquiring responses, a consumed cost can not but be further increased. In addition, when the number of sensor systems is increased as described above, a significant large amount of response data output from a plurality of sensors is transmitted to a main computer to cause an overload, such that loss of the data is caused or the data is not normally processed. The above Related Art Documents do not suggest an effective method for solving these problems.

Therefore, a technology capable of being more economic, effectively decreasing an amount of dynamic response data, and securing reliability of data in building the SHM system in the constructional structure has been demanded.

RELATED ART DOCUMENT

Patent Document

1. Korean Patent Laid-Open Publication No. 2010-0002686 entitled "System for Measuring and Controlling Structure Using Bidirectional Communication Function", published on Jan. 7, 2010
2. Korean Patent No. 0512123 entitled "Structure Monitoring System Using Smart Wireless Measuring System", registered on Aug. 26, 2005
3. U.S. Patent Application Publication No. 2010-0238027 entitled "Device for Monitoring the Health Status of Structures", published on Sep. 23, 2010

SUMMARY

An embodiment of the present invention is directed to providing a wireless measuring system based on a cochlea principle for acquiring a dynamic response of a constructional structure capable of decreasing a system building cost and being easily maintained by wirelessly transmitting dynamic response data of the constructional structure.

Another embodiment of the present invention is directed to providing a wireless measuring system capable of decreasing an amount of transmission data and wirelessly transmitting reliable data without substantial loss of effective data by applying a principle in which a cochlea recognizes a sound in a process of efficiently processing obtained dynamic response data.

Still another embodiment of the present invention is directed to providing a wireless measuring system capable of easily changing a design and implementing a new function by encoding and embedding a dynamic response data compressing process as a computer program.

In one general aspect, a wireless measuring system based on a cochlea principle for acquiring a dynamic response of a constructional structure in order to evaluate health and a state of the constructional structure, includes: a sensing unit including an acceleration sensor sensing vibrations of the constructional structure and deconstructing measured signals output from the acceleration sensor and having frequency components for each specific frequency component, reconstructing the deconstructed signals, and then sampling and compressing only peaks; and a main computer receiving the measured signals compressed by the sensing unit and monitoring and analyzing the health and the state of the constructional structure, wherein the sensing unit and the main computer transmit and receive signals using a wireless transmitting and receiving means.

The sensing unit may have a program embedded therein, the program being to perform: a deconstructing process of extracting signals in specific frequency ranges from the measured signals output from the acceleration sensor using a band pass filter unit including a plurality of band pass filters having different central frequencies or bandwidths, a reconstructing process of reconstructing filtered signals based on the central frequencies and the bandwidths of the plurality of band pass filters, and a compressing process of sampling peak data by applying a peak picking algorithm to the reconstructed signals.

The sensing unit may calculate a reconstruction error J and allow the central frequencies and the bandwidths of the band pass filters to be determined based on the calculated reconstruction error, and may calculate a reconstruction error J to a data compression rate (CR) and allow the number of band pass filters to be determined based on the calculated reconstruction error to the data compression rate.

The main computer may apply a programmed control algorithm to the measured signals transmitted from the sensing unit to generate a feedback signal controlling the sensing unit and may transmit the feedback signal to the sensing unit through the wireless transmitting and receiving means to control the sensing unit.

The wireless measuring system based on a cochlea principle for acquiring a dynamic response of a constructional structure may further include a damper connected to the sensing unit, attached to the constructional structure, and damping vibrations, wherein the main computer allows a signal driving the damper to be included in the feedback signal in order to damp the vibrations of the constructional structure.

The wireless measuring system based on a cochlea principle for acquiring a dynamic response of a constructional structure may further include a power supplying unit for supplying power to the sensing unit, wherein the power supplying unit uses self power generation or uses any one of environment-friendly energy sources including a solar heat source, a wind force source, and a vibration source.

BRIEF DESCRIPTION OF THE DRAWINGS

FIG. 3A is a diagram showing a person's ear.

FIG. 3B is an enlarged view of a cochlea in FIG. 3A.

FIG. 6 is a diagram showing an example of calculating a reconstruction error depending on an interval between band pass filters and bandwidths of the band pass filters.

[Detailed Description of Main Elements]

| | |
|---|---|
| 10: Acceleration sensor | 20: Wireless transmitting and receiving means |
| 30: Damper | 100: Sensing unit |
| 110: Band pass filter unit | 120: ADC |
| 130: DAC | 200: Main computer |

DETAILED DESCRIPTION OF EMBODIMENTS

Figure 1:
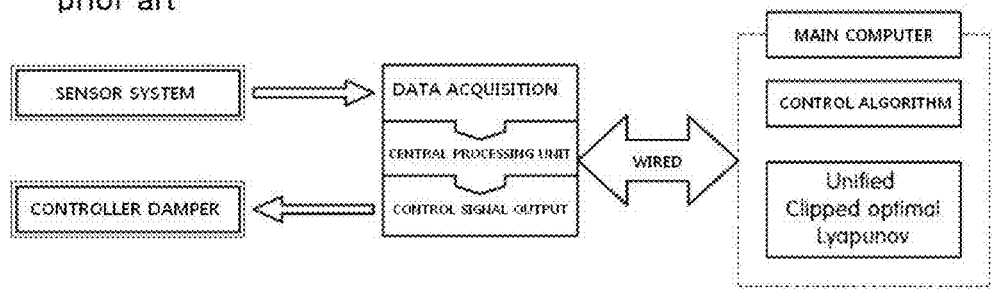
FIG. 1 is a configuration diagram of a system of measuring and controlling a structure according to the related art.
Figure 2:
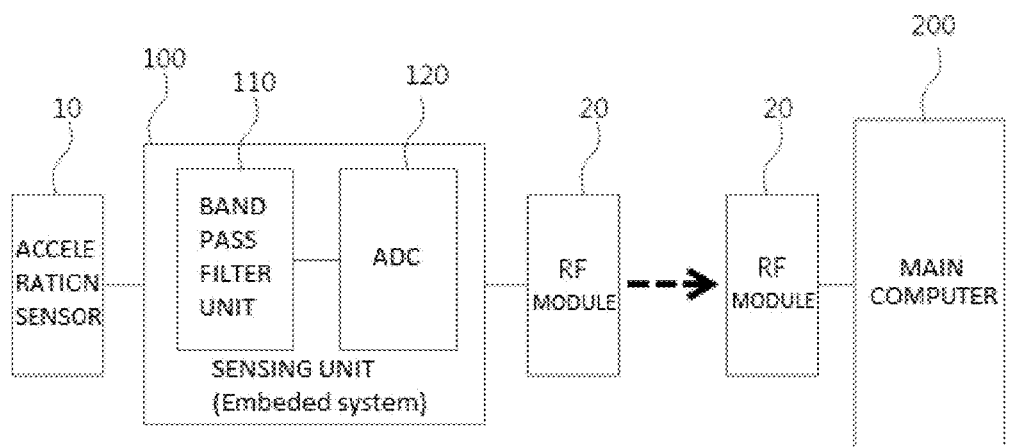
FIG. 2 is a configuration diagram showing a wireless measuring system according to a first exemplary embodiment of the present invention.

FIG. 2 is a configuration diagram showing a wireless measuring system according to a first exemplary embodiment of the present invention. Referring to FIG. 2, a system of measuring a dynamic response for evaluating health and a state of a constructional structure is mainly configured to include a sensing unit 100 and a main computer 200, wherein the sensing unit 100 and the main computer 200 transmit and receive signals and data using a wireless transmitting and receiving means 20. Here, a radio frequency (RF) module, or the like, may be used as the wireless transmitting and receiving means 20.

The sensing unit 100 includes an acceleration sensor 10 sensing vibrations of the constructional structure and serves to deconstruct measured signals output from the acceleration sensor 10 and having frequency components for each specific frequency component, reconstruct the deconstructed signals, and then sample and compress only peaks, and the main computer 200 receives the measured signals compressed by the sensing unit 100 and serves to monitor and analyze health and a state of the constructional structure.

Particularly, the sensing unit 100 performs "deconstruction-reconstruction-compression" processes in order to efficiently transmit the signal output from the acceleration sensor 10 to the main computer 200.

Hereinafter, a data processing process of the sensing unit 100 will be described in more detail with reference to the accompanying drawings.

In an exemplary embodiment of the present invention, in an efficient data processing process, a principle in which a sound is recognized by a cochlea of a human body has been applied. Therefore, before describing a data processing process according to an exemplary embodiment of the present invention, a process in which a sound is recognized by a cochlea will be described.

FIG. 3A is a diagram showing a person's ear; and FIG. 3B is an enlarged view of a cochlea in FIG. 3A. As shown in FIG. 3B, the cochlea has a basement membrane to a cerebrum cortex spatially arranged with respect to frequencies, and has a tonotopy arrangement maximally reacting to a specific frequency depending on each position. A unique vibration principle of only the basement membrane is that different portions of the base membrane vibrate depending on frequencies of sound energy. Therefore, the sound is deconstructed into signals corresponding to the respective frequency bands in the cochlea, peaks of the deconstructed signals are encoded by an inner hair cell, and the encoded signals are transmitted to a cerebrum. In this case, the cerebrum reads a magnitude of the signal to recognize the sound.

A biological neural system as described above provides a potential solution in designing the wireless measuring system according to an exemplary embodiment of the present invention.

Figure 4:
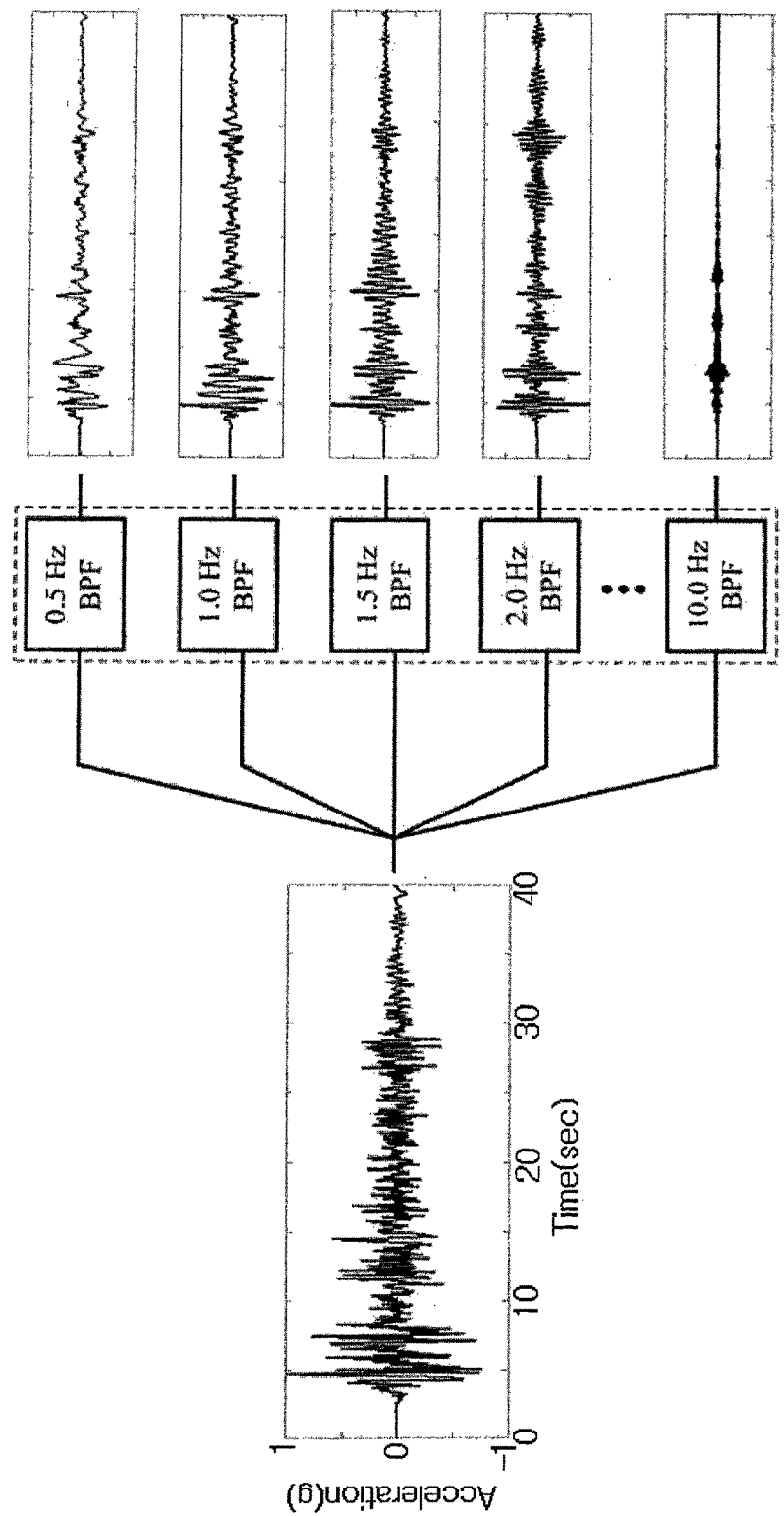
FIG. 4 is a diagram showing a process in which a measured signal is deconstructed through a band pass filter unit.

FIG. 4 is a diagram showing a process in which a measured signal is deconstructed through a band pass filter unit 110. As shown in FIG. 4, the deconstructing process is a process of extracting signals in a central frequency or specific frequency ranges through the band pass filter unit 110 including a plurality of band pass filters having different bandwidths from the measured signals output from the acceleration sensor 10 of the sensing unit 100. Since the band pass filters have been designed so as to pass only defined frequency regions therethrough, complicated measured signals pass through band pass filters corresponding to pass bands thereof.

In the case of a civil engineering structure having a relatively low natural frequency of 10 Hz or less, a central frequency of the band pass filter is limited to a frequency of 0.1 to 10 Hz at the time of designing the band pass filter unit 110. In detail, for example, as shown in FIG. 4, when a central frequency is 0.5, 1.0, 1.5, . . . , 10.0 Hz, an interval between band pass filters is 0.5 Hz and the number of band pass filters is 20.

Figure 5:
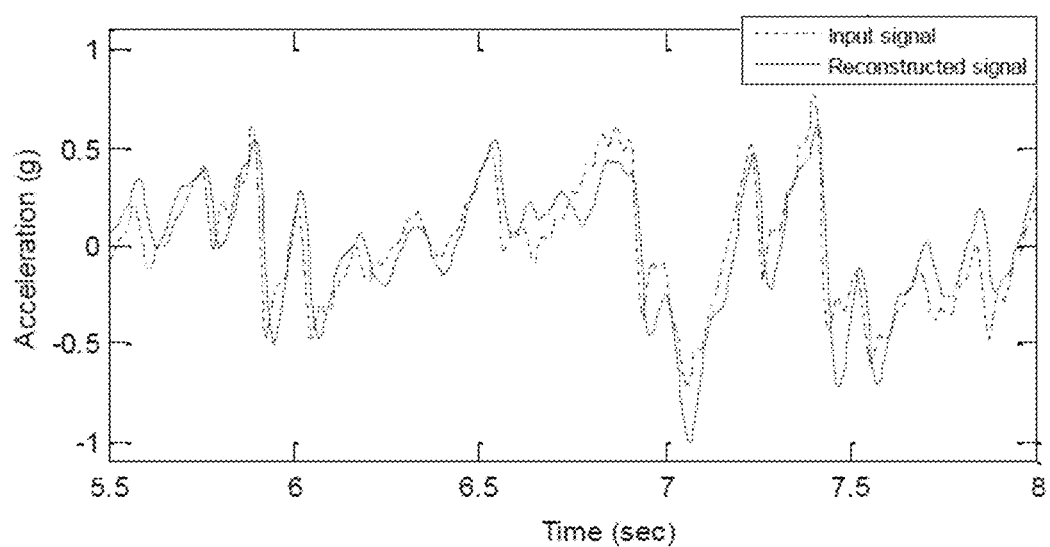
FIG. 5 is a diagram showing a comparison result between an original signal and a signal deconstructed and reconstructed through the band pass filter unit of FIG. 4.

Then, a reconstructing process of reconstructing the filtered signals based on central frequencies and bandwidths of the plurality of band pass filters is performed. For reference, a comparison result between an original signal and a signal deconstructed and reconstructed through the band pass filter unit 110 of FIG. 4 is shown in FIG. 5.

Here, the sensing unit 100 may calculate a reconstruction error J using the following Equation 1, and the smaller the reconstruction error J, the higher the reconstruction rate of the signal.

$$\text{Reconstruction Error}(J) = \frac{\int_0^T (u(t) - y(t))^2}{T} \quad \text{[Equation 1]}$$

Here, u(t) indicates an original signal, y(t) indicates a reconstructed signal, and T indicates a total measurement time.

Preferably, central frequencies and bandwidths of appropriate band pass filters need to be determined in the deconstructing process based on the calculated reconstruction error J. In other words, the reconstruction error is calculated while changing the central frequencies and the bandwidths of the respective band pass filter, and the central frequencies and the bandwidths of the band pass filters when the reconstruction error is the smallest are determined. An example of calculating a reconstruction error J depending on an interval between band pass filters of the band pass filter unit including ten band pass filters (interval between central frequencies) and bandwidths of the band pass filters is shown in FIG. 6. As shown in FIG. 6, the smallest value of the reconstruction error is 0.054 (denoted by a circle). In this case, an interval between the band pass filters and a bandwidth of the band pass filters are 0.9 and 0.6, respectively, or are 1.0 and 0.7, respectively.

Figure 7:
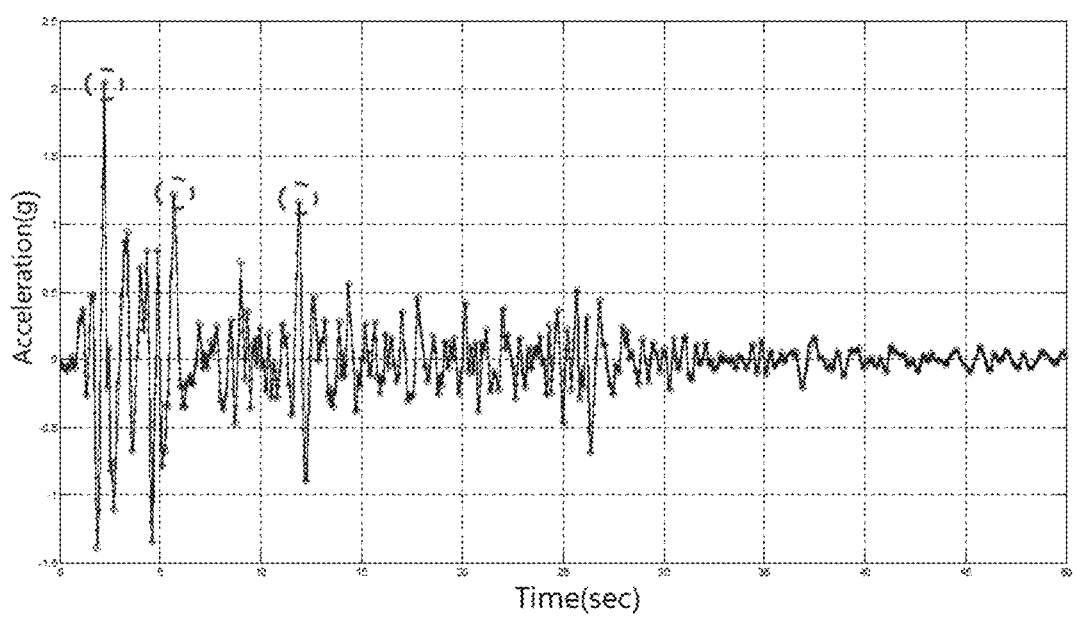
FIG. 7 is a diagram showing an example of a process of detecting a peak by applying a peak value picking algorithm to a reconstructed signal.

A final process is a compressing process of sampling peak data by applying a peak picking algorithm to the reconstructed signals, which is shown in FIG. 7. The peak picking algorithm indicates an algorithm for minimizing an amount of transmission data by detecting only peaks of the reconstructed signal. In more detail, the peak data (denoted by a circle in FIG. 7) are detected depending on a preset sampling rate using an analog to digital converter (ADC) 120, the detected peak data are digitized, and the digitized data are transmitted to the main computer 200 in real time through the wireless transmitting and receiving means 20.

Here, a data compression ratio (CR) is calculated using the following Equation 2.

$$\text{Compression Ratio}(CR) = \frac{NB_c}{NB_s} \quad \text{[Equation 2]}$$

Here, NBC indicates the number of peaks of the reconstructed signal, and NBS indicates the number of peaks of the original signal.

Figure 8:
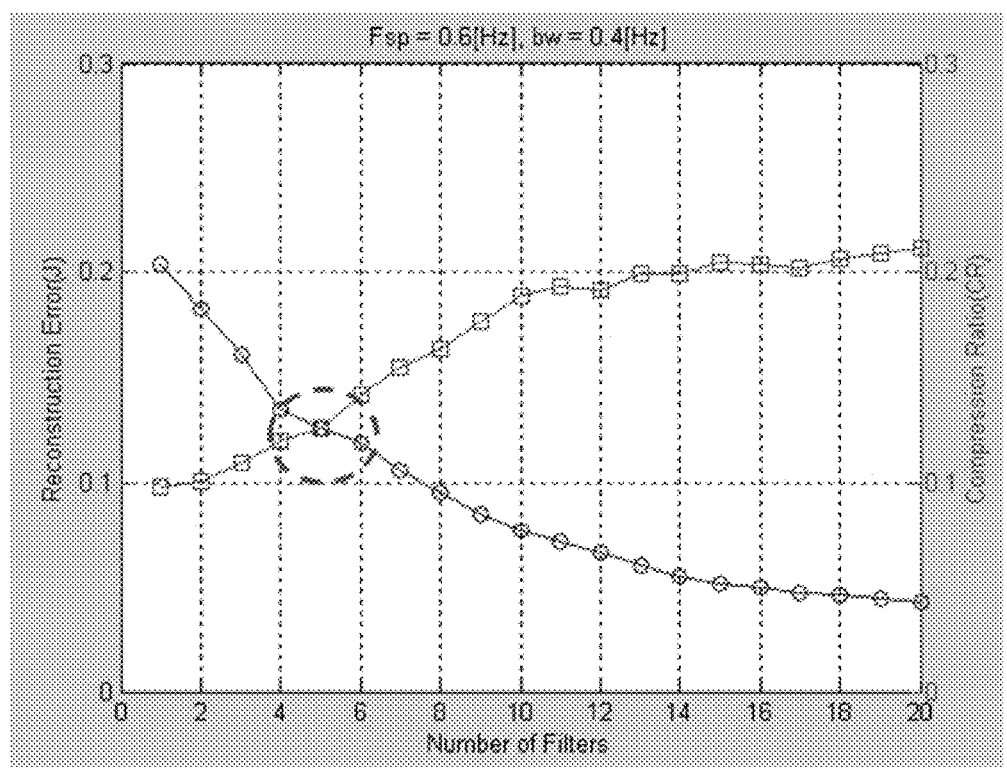
FIG. 8 is a diagram showing an example of determining the number of band pass filters through a reconstruction error and a data compression ratio.

Here, the number of peaks of the original signal may be obtained by applying Nyquist sampling theory. The number of band pass filters used in the deconstructing process is determined using the calculated data compression ratio (CR) and reconstruction error J value. In detail, as described above, it is preferable to determine the optimized number of band pass filters by evaluating the reconstruction error J value to the data compression ratio (CR) while increasing or decreasing the number of band pass filters of which the central frequencies and the bandwidths are determined through the reconstruction error J value. FIG. 8 is a diagram showing an example of determining the number of band pass filters through a reconstruction error and a data compression ratio. It may be seen that an interval Fsb between the band pass filters is 0.6 Hz, a bandwidth bw of the band pass filters is 0.4 Hz, and as the number of band pass filters is increased, a reconstruction error J is decreased, but a compression ratio (amount of data) is increased. That is, when the number of band pass filters is increased, a more perfect signal may be reconstructed. However, the increase in the number of band pass filters directly leads to an increase in a system building cost and an amount of data.

In summary, since the increase in the number of band pass filters always leads to increasing the compression ratio simultaneously with decreasing the reconstruction error, the number of band pass filters needs to be determined so that loss of effective information and an appropriate compression ratio are traded off. As shown in FIG. 8, it is preferable to select the number of band pass filters at a crossed portion between the reconstruction error J and the data compression ratio (CR) graphs.

In an exemplary embodiment of the present invention, the dynamic response data processing process is encoded as a computer program and is embedded in the sensing unit 100 to thereby be configured in a software form. In an exemplary embodiment of the present invention, all data processing processes in which the signal is deconstructed and reconstructed through the band pass filter unit 110 and is compressed using the ADC 120, and an algorithm of calculating the reconstruction error J and the data compression ratio (CR) and determining the central frequencies, the bandwidths, and the number of the plurality of band bass filters configuring the band pass filter unit 110 based on the calculated reconstruction error J and data compression ratio (CR) are configured in a software form, such that temporal and economic gains may be present as compared with the case in which they are configured in a hardware form and a design condition for optimizing the data processing process may be easily changed. In addition, a new function may be readily implemented, and software may be flexibly changed depending on various measuring conditions.

In an exemplary embodiment of the present invention, the data transmitted from the sensing unit 100 to the main computer 200 through the process as described above are analyzed by a programmed control algorithm of the main computer 200, such that health and a state of the constructional structure may be monitored in real time (unidirectional wireless measuring system).

Figure 9:
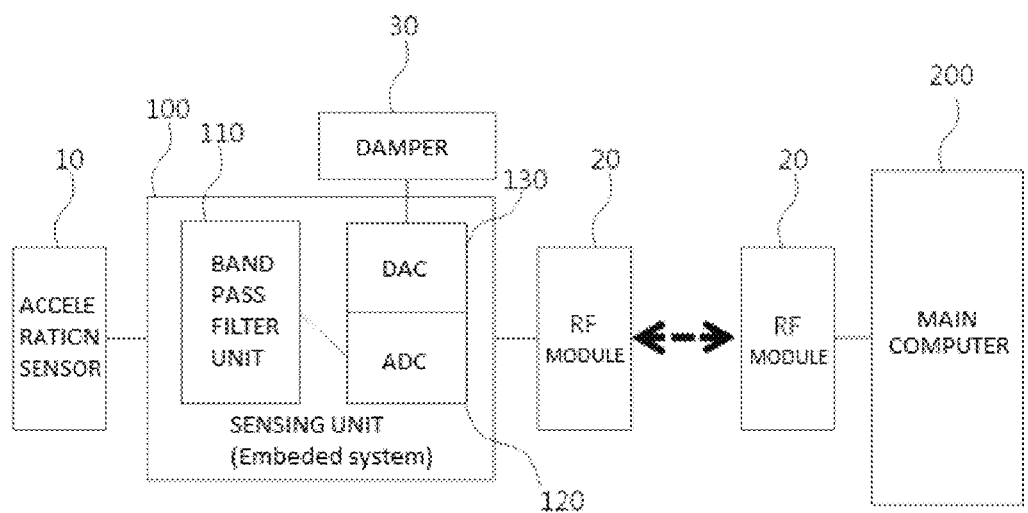
FIG. 9 is a configuration diagram showing a wireless measuring system according to a second exemplary embodiment of the present invention.

In addition, as shown in FIG. 9, which is a configuration diagram showing a wireless measuring system according to a second exemplary embodiment of the present invention, the main computer 200 may also apply a programmed control algorithm to the measured signals transmitted from the sensing unit to generate a feedback signal controlling the sensing unit 100 and transmit the feedback signal to the sensing unit 100 through the wireless transmitting and receiving means 20 to control the sensing unit 100 (bidirectional wireless measuring system). For example, a control for switching the sensing unit 100 into a measuring standby mode and performing measurement for only a set time or turning on/off power in order to minimize power consumption is performed.

Meanwhile, in an exemplary embodiment of the present invention, as shown in FIG. 9, a damper 30 connected to the sensing unit 100, attached to the constructional structure, and damping vibrations may be further included. Here, the main computer 200 allows a signal driving the damper 30 to be included in the feedback signal and transmits the feedback signal including the signal driving the damper 30 to the sensing unit 100, and the damper 30 is driven in order to damp the vibrations of the constructional structure.

For example, there is a method of setting a frequency to a multiple to cause damping, thereby offsetting the vibrations of the constructional structure. In this case, the sensing unit 100 further includes a digital to analog converter (DAC) 130 converting the feedback signal transmitted from the main computer 200 into an analog signal to drive the damper 30.

In addition, in an exemplary embodiment of the present invention, a power supplying unit (not shown) for supplying power to the sensing unit 100 is further included. The power supplying unit may use self power generation or use any one of environment-friendly energy sources including a solar heat source, a wind force source, and a vibration source.

Figure 10:
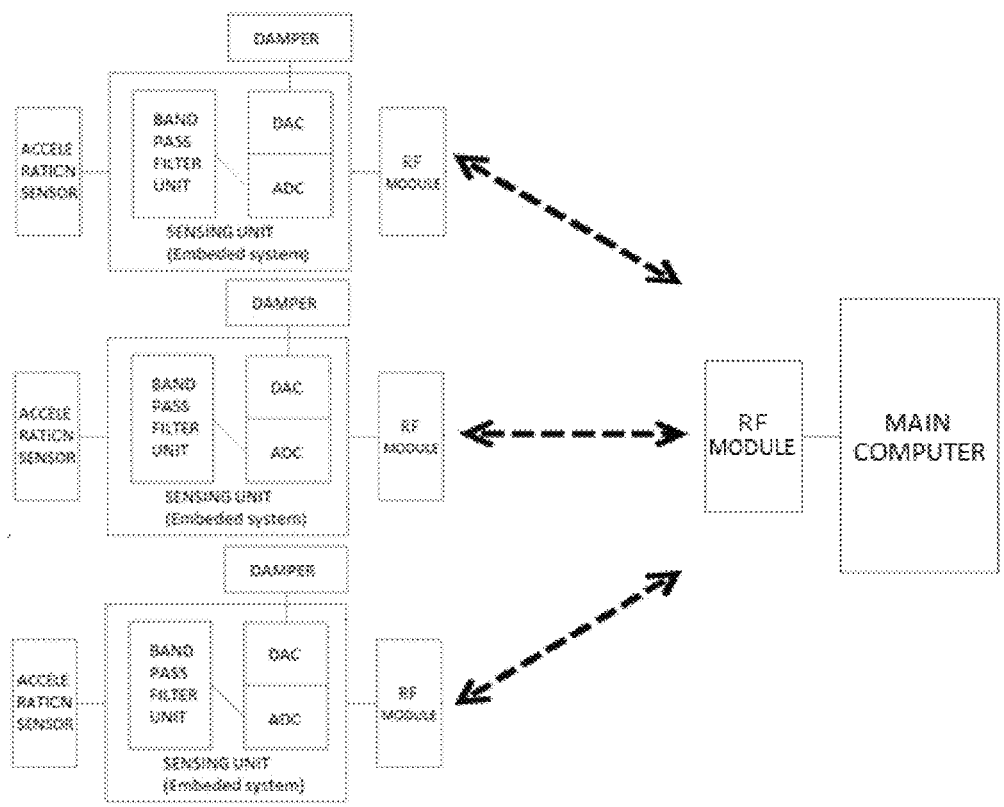
FIG. 10 is a diagram showing a wireless measuring system including a plurality of sensing units according to an exemplary embodiment of the present invention.

FIG. 10 is a diagram showing a wireless measuring system including a plurality of sensing units 100 according to an exemplary embodiment of the present invention. The plurality of sensing units 100 may be installed at various measuring points. In an exemplary embodiment of the present invention, since the plurality of sensing units 100 effectively compress the dynamic response data transmitted to the main computer 200 and wirelessly transmit the compressed data, the number of measuring points is increased, such that effective data are hardly lost.

As described above, in an exemplary embodiment of the present invention, which is a wireless measuring system based on a cochlea principle for acquiring a dynamic response of a constructional structure, a building cost and a maintenance cost may be decreased unlike an existing wired connection system, reliable data may be acquired while decreasing a significant large amount of response data output from the plurality of sensors through the data processing process using the principle in which the sound is recognized by the cochlea, and the constructional structure may be monitored and controlled in real time without an overload of the system.

As set forth above, in an exemplary embodiment of the present invention, which is a wireless measuring system based on a cochlea principle for acquiring a dynamic response of a constructional structure, a building cost and a maintenance cost may be decreased unlike an existing wired connection system, reliable data may be acquired while decreasing a significant large amount of response data output from the plurality of sensors through the data processing process using the principle in which the sound is recognized by the cochlea, and the constructional structure may be monitored and controlled in real time without an overload of the system.

In addition, in an exemplary embodiment of the present invention, the dynamic response data processing process is made as a program and is embedded in the sensing unit to thereby be configured in a software form, such that temporal and economic gains may be present as compared with the case in which they are configured in a hardware form and a design condition for optimizing the data processing process may be easily changed. Further, a new function may be readily implemented, and software may be flexibly changed depending on various measuring conditions.

The accompanying drawings are only examples shown in order to describe the technical idea of the present invention in more detail. Therefore, the technical idea of the present invention is not limited to shapes of the accompanying drawings.

In addition, the present invention is not limited to the above-mentioned exemplary embodiments, and may be variously applied, and may be variously modified without departing from the gist of the present invention claimed in the claims.

What is claimed is:

1. A wireless measuring system based on a cochlea principle for acquiring a dynamic response of a constructional structure in order to evaluate health and a state of the constructional structure, comprising:
   a sensing unit comprising a processor including an embedded computer software program for deconstructing measured signals output from an acceleration sensor into a plurality of frequency ranges, reconstructing the deconstructed signals to form a reconstructed signal, sampling only peaks of the reconstructed signal, compressing the peaks of the reconstructed signal, and digitizing the compressed peaks of the reconstructed signal; and
   a main computer receiving from the sensing unit the digitized compressed peaks of the reconstructed signal, the main computer including a programmed control algorithm for monitoring and analyzing the health and the state of the constructional structure based on the received digitized compressed peaks of the reconstructed signal,
   wherein the sensing unit and the main computer transmit and receive signals using a wireless transmitting and receiving means,
   wherein:
   deconstructing the measured signals includes extracting signals in specific frequency ranges from the measured signals output from the acceleration sensor using a plurality of band pass filters having different central frequencies or bandwidths,
   reconstructing the deconstructed signals includes reconstructing the extracted signals based on the central frequencies and the bandwidths of the plurality of band pass filters,
   sampling only peaks of the reconstructed signal includes sampling peak data by applying a peak picking algorithm to the reconstructed signal,
   the embedded computer software program calculates a reconstruction error (J) while changing the central frequencies or the bandwidths to determine the central frequencies or the bandwidths used in the deconstructing when the reconstruction error is the smallest, and
   the embedded computer software program calculates a data compression rate (CR) and the reconstruction error (J) while changing the number of band pass filters to determine the number of band pass filters used in the deconstructing when a difference between the data compression rate (CR) and the reconstruction error (J) is the smallest.

2. The wireless measuring system based on a cochlea principle for acquiring a dynamic response of a constructional structure of claim 1, further comprising a power supplying unit for supplying power to the sensing unit,
   wherein the power supplying unit uses self power generation or uses any one of environment-friendly energy sources including a solar heat source, a wind force source, and a vibration source.

3. The wireless measuring system based on a cochlea principle for acquiring a dynamic response of a constructional structure of claim 1, wherein the programmed control algorithm generates a feedback signal controlling the sensing unit and transmits the feedback signal to the sensing unit through the wireless transmitting and receiving means to control the sensing unit based on the digitized compressed peaks of the reconstructed signal.

4. The wireless measuring system based on a cochlea principle for acquiring a dynamic response of a constructional structure of claim 3, further comprising a damper connected to the sensing unit, attached to the constructional structure, and operative for damping vibrations of the constructional structure,
   wherein the main computer allows a signal driving the damper to be included in the feedback signal in order to damp the vibrations of the constructional structure.

* * * * *